United States Patent [19]

Houston et al.

[11] Patent Number: 5,181,925

[45] Date of Patent: Jan. 26, 1993

[54] FEMORAL COMPONENT FOR A KNEE JOINT PROSTHESIS HAVING A MODULAR CAM AND STEM

[75] Inventors: Michelle L. Houston, Winona Lake; Kevin M. Greig, Leesburg, both of Ind.

[73] Assignee: Zimmer, Inc., Warsaw, Ind.

[21] Appl. No.: 833,254

[22] Filed: Feb. 10, 1992

Related U.S. Application Data

[63] Continuation of Ser. No. 690,191, Apr. 22, 1991, abandoned.

[51] Int. Cl.$^5$ ................................................ A61F 2/38
[52] U.S. Cl. ........................................ 623/20; 623/18
[58] Field of Search ................................. 623/20, 18

[56] References Cited

FOREIGN PATENT DOCUMENTS 0376658 4/1990 European Pat. Off. .............. 623/20

Primary Examiner—David Isabella
Assistant Examiner—Debra S. Brittingham
Attorney, Agent, or Firm—Todd A. Dawson

[57] ABSTRACT

A femoral component for a knee joint prosthesis having a modular cam which may be connected intraoperatively to provide posterior tibial subluxation resistance when the posterior cruciate ligament is sacrificed. The cam includes protrusions which engage with notches on the stem base to prevent rotation of the cam during use. A stem extension is connected to the stem base for clamping engagement of the cam body therebetween. A transverse opening may be formed in the stem base for providing access to the stem extension threads. The threads may then be malformed to prevent rotation of the stem extension relative to the extension.

3 Claims, 3 Drawing Sheets

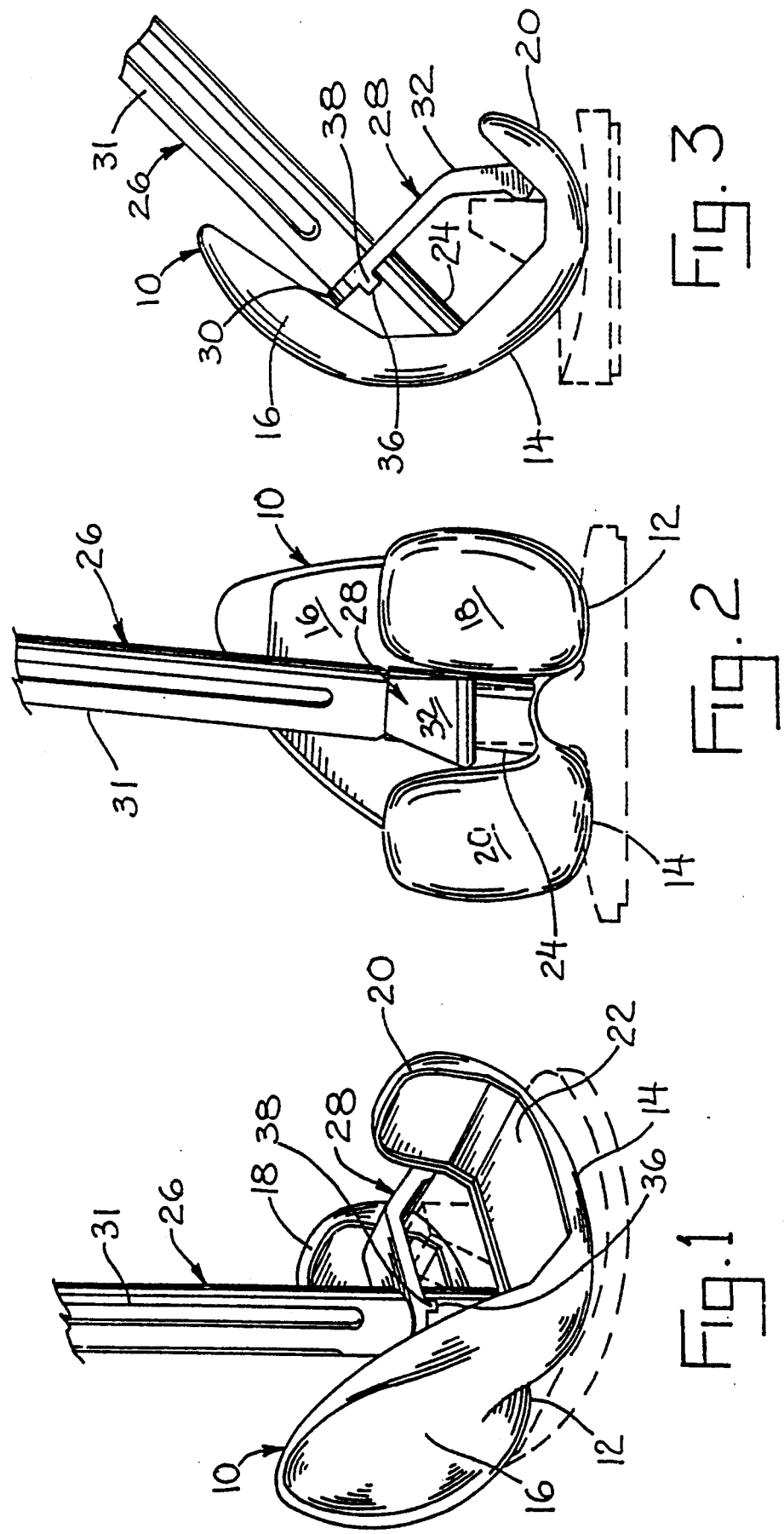

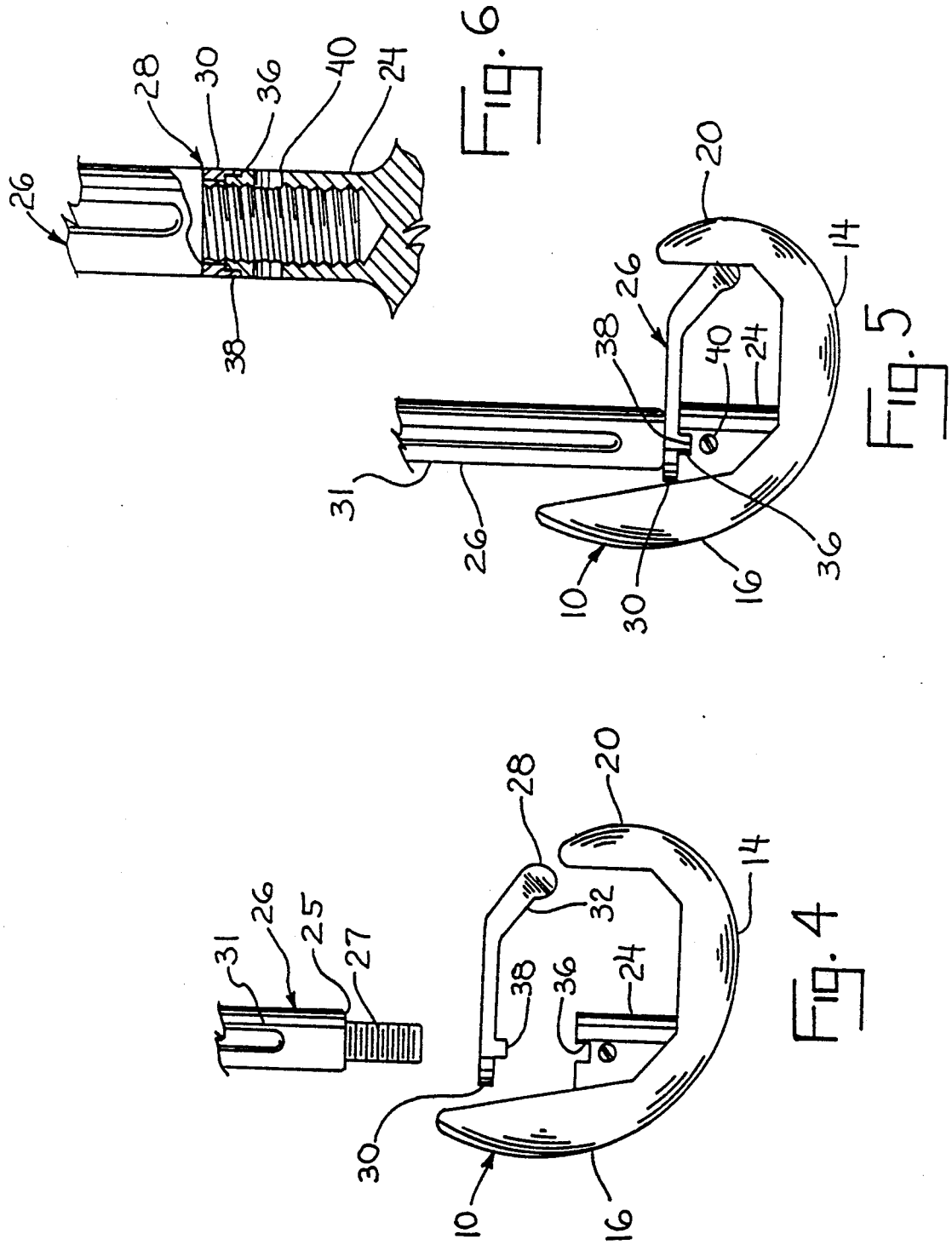

1

FEMORAL COMPONENT FOR A KNEE JOINT PROSTHESIS HAVING A MODULAR CAM AND STEM

This is a continuation of application Ser. No. 07/690,191 filed Apr. 22, 1991, now abandoned.

FIELD OF THE INVENTION

This invention relates to a femoral component of a knee joint prosthesis and has specific relevance to a femoral component having a modular cam for providing posterior tibial subluxation resistance when the posterior cruciate ligament is removed.

BACKGROUND OF THE INVENTION

When performing a total knee arthroplasty it is beneficial to intraoperatively decide on the viability of the posterior cruciate ligament. If the posterior cruciate ligament is functional then a knee joint prosthesis utilizing the ligament may be used. If, however, the ligament is non-functional and is removed, a posterior cruciate ligament substituting prosthetic knee joint may be desired to provide posterior tibial subluxation resistance.

Heretofore, to accommodate the intraoperative decision described above, two separate femoral components were required to be kept within the operating arena. One solution to this problem is addressed in U.S. Pat. No. 4,950,298. The '298 patent discloses a modular knee joint prosthesis wherein an augmentation plate may be connected during surgery to the femoral contact surface of a femoral component. The plate provides augmentation for the distal end of the femur and includes a triangle stop and transverse post which engages a ramp post on the tibial articulating surface to limit undesirable movement. A problem with the '298 patent is that the modular plate component combines the distal augmentation with the triangle stop and there may be instances where posterior subluxation resistance may be desirable without distal augmentation of the femur.

SUMMARY OF THE INVENTION

The femoral component for a knee joint prosthesis of this invention eliminates the problems above by providing a modular cam which may be connected intraoperatively to the femoral component to engage a spine on the tibial articulate surface to provide posterior tibial subluxation without providing distal augmentation of the femur. The cam includes a body having an opening therethrough to accommodate a threaded portion of a stem extension and a cam bar extending therefrom. The stem extension is turned into an internally threaded stem base on the femoral component to secure the cam body therebetween. The cam bar extends in the direction of the posterior condyles and engages the tibial articulating surface to limit movement of the femoral component relative to the articulating surface. The stem extension may be formed in a variety of lengths, or shapes.

In the preferred embodiment, the stem extension is secured against rotation relative to the stem by the use of locking threads on the post. Alternatively, a through bore may be transverse to the stem of the femoral component and in communication therewith, the transverse bore providing access to a portion of the threads on the stem extension when seated. A thread deforming tool engages a portion of the threads through the transverse bore to deform a portion of the threads to an extent that rotation of the stem extension in either direction is prohibited. Rotation of the cam relative to the femoral component is prevented by mutually engaging splines and grooves.

BRIEF DESCRIPTION OF THE DRAWINGS

FIG. 1 is a perspective view of the femoral component, cam, and stem extension of the preferred embodiment with a tibial articulate surface shown in broken lines for illustrative purposes only.

FIG. 2 is a rear end elevational view of FIG. 1.

FIG. 3 is a side elevational view FIG. 1.

FIG. 4 is an exploded view of FIG. 3.

FIG. 5 is a sectional view of the invention illustrating an alternative method of securing the post extension to the femoral component.

FIG. 6 is a partial sectional view of FIG. 4.

DESCRIPTION OF THE PREFERRED EMBODIMENTS

Figure 9:
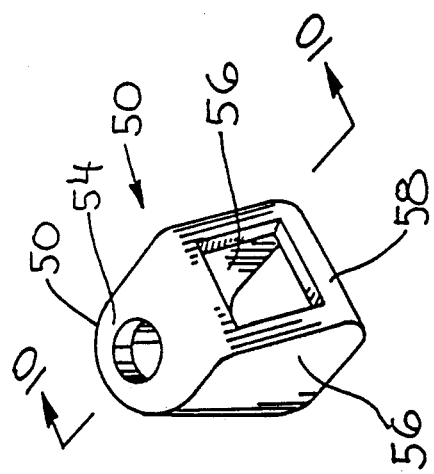
FIG. 9 is a perspective view of a third alternative embodiment of the cam of the invention.

The preferred embodiments herein described are not intended to be exhaustive or to limit the application to the precise forms disclosed. Rather, they are chosen and described so that others skilled in the art might utilize the teachings contained herein.

Referring now to the drawings, femoral component 10 is illustrated as including a pair of convex articular surface defining elements 12, 14 which are connected by a anteriorly situated patellar plate portion 16 comprising a bridge. The convex articular surfaces are separated by a slot defined by laterally disposed condyles 18, 20. The femoral component also defines a femoral bone contact surface 22. A stem base 24 extends upwardly from the femoral contact surface 22 adjacent patellar plate portion 16 and is integral with component 10. Stem base 24 is internally threaded and includes a plurality of notches 36 (only one shown) formed in its upper surface.

A stem extension 26 is provided and includes a male threaded end 27 and a non-threaded end 31. Stem extension 26 is provided for insertion into the intramedullary canal of the femur. In practice, stem extension 26 may be of any desired length. It is most likely that a plurality of stem extensions having a variety of lengths will be available during surgery to accommodate an intraoperative decision by the surgeon on the appropriate stem length. Alternatively, a locking cap (not shown) may be turned into stem base 24 when an extension is not required. Stem extension 26 is turned into threaded stem base 24 of the femoral component for connection of the two stem portions. To prevent stem extension 26 from turning out of stem base 24, the threaded portions of stems 24 and 26 are formed with anti-reversible threading or locking threads as are known in the industry.

Cam 28 includes as integral components a body 30 and a cam bar 32. An opening 34 is formed through cam body 30. In the preferred embodiment, the end of cam bar 32 spaced from opening 34 is inclined as illustrated in the figures. Cam 28 is connected to the femoral component, at the option of the surgeon, by first aligning opening 34 of cam 28 with the open end of stem base 24.

The male threaded end 27 of stem extension is inserted into and turned within stem base 24 until the shoulder 25 of stem extension 26 compressively contacts the body of cam 28 about opening 34. As mentioned, the screw threads on stem extension 26 and those formed in stem base 24 may be formed to constitute a locking mechanism to secure stem extension 26 against rotation once seated. When connected to the femoral component in the manner described, cam bar 32 extends towards condyles 12 and 14 for contact with the spine of a tibial articulate surface (shown in broken lines only) to limit posterior subluxation of the tibia (see FIG. 3). A pair of protrusions 38 (only one shown) extend from cam body 30 in a downward direction as shown in FIG. 1 in mating engagement with the notches in stem base 24 to prevent rotation of the cam relative to the femoral component. In practice, protrusions 38 seat within notches 36 with close tolerance to prevent cam 28 from axially rotating. The clamping engagement of the cam body between shoulder 25 of stem extension 26 and the upper surface of stem base 24 prevents inferior-superior movement of the cam.

An alternative embodiment of the femoral component of the invention is illustrated in FIGS. 5 and 6. In the alternative embodiment a pair of openings 40 are formed in stem base 24 transverse to its central opening. In use, after the stem extension 26 has been secured to femoral component 10 in the manner described above, the surgeon, deforms the threads of stem extension 26 aligned with openings 40 to such an extent that rotation of the stem in either direction is prevented. It is anticipated that, in use, a tool resembling a clamp will be developed for engagement with the openings 40 to provide sufficient mechanical force to deform the threads. Alternatively, a punch type device may be employed to deform the male threads when struck.

It should be understood that the femoral component and stem extension of the invention may be used with or without the cam. The determination of whether the cam is required for a particular patient may be made intraoperatively by the surgeon prior to implanting the device.

Figure 7:
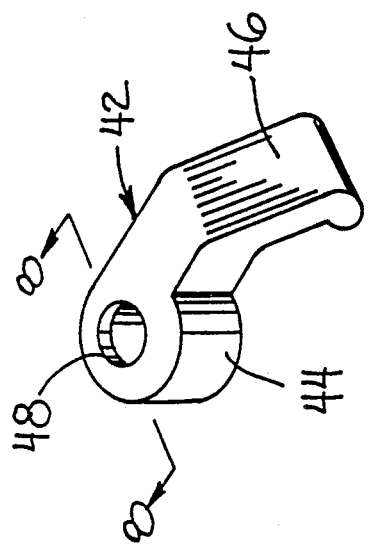
FIG. 7 is a perspective view of an alternative embodiment of the cam of the invention.
Figure 8:
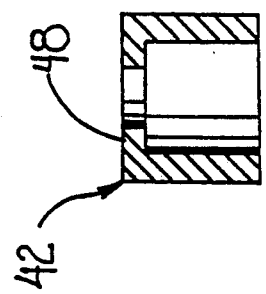
FIG. 8 is a sectional view taken along line 8—8 of FIG. 7.

An alternative embodiment of the cam of the invention is illustrated in FIGS. 7 and 8. Cam 42 includes a cylindrical body 44 with an arm 46 extending outwardly therefrom for contact with the spine of a tibial articulate surface to limit posterior subluxation of the tibia. An upper wall 48 is formed in body 44 and constitutes a shoulder. In use, the cylindrical body of cam 42 slides around the outer periphery of the femoral stem in close tolerance therewith until shoulder 48 contacts the upper surface of the stem. The stem base of the femoral component is slightly spaced from the patellar plate to accommodate the cylindrical body of the cam thereabout. A stem extension is turned into the femoral stem in keeping with the above disclosure to secure the cam to the femoral component. The femoral component and stem extension are not illustrated in FIGS. 7 and 8 as it is thought to be understood and redundant when taken with the above disclosure regarding FIGS. 1-6.

Figure 10:
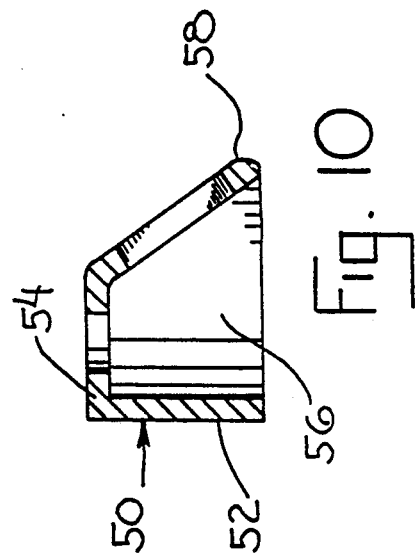
FIG. 10 is a sectional view taken along line 10—10 of FIG. 9.

A second alternative embodiment of the cam of the invention is illustrated in FIGS. 9 and 10. Cam 50 of FIGS. 9 and 10 is substantially similar to the cam of FIGS. 7 and 8 described above. Cam 50 includes a cylindrical body 52 having a upper end wall 54 with an opening therethrough for accommodating the threaded end of a stem extension (not shown). A pair of side walls 56 extending parallel and outwardly therefrom. Side walls 56 are interconnected by a cross bar 58. Cross bar 58 is adapted to contact the spine of a tibial articulate surface to limit posterior subluxation of the tibia As with cam 42 of FIGS. 7 and 8, the cylindrical body of cam 50 is slide over a stem of a femoral component until the upper surface of the stem contacts wall 54. The stem extension is turned into the femoral stem as described above. The side walls 56 of the cam may provide lateral stability to the knee joint by contacting the side walls of the tibial articulate spine (not shown) Anterior femoral movement is limited by contact between the spine and cross bar 58. As with FIGS. 7 and 8, the knee joint including a tibial articulate surface and femoral component are not illustrated in the interest of brevity but it is believed that the above descriptions provide a full and complete disclosure of the invention.

It should be also be understood that the invention is not to be limited by the precise form disclosed but rather may be modified within the scope of the appended claims.

We claim:

1. A modular cam for selective connection to a femoral component having a pair of spaced condyles adapted to contact a tibial component in an articulating manner, said modular cam having an elongated body terminating at opposite ends, said body having means on one end for connection to said femoral component, said body configured to extend between said condyles at said opposite end and engage a portion of said tibial component during articulation of said femoral component to thereby limit movement of said femoral component relative to said tibial component.

2. The modular cam of claim 1 wherein said cam body is compact.

3. The cam of claim 1 wherein said body is adapted for clamping engagement between mutually cooperating portions of said femoral component such that a portion said body extends rearwardly between condyles of said femoral component.

* * * * *